United States Patent [19]

Ludwig

[11] Patent Number: 5,252,192
[45] Date of Patent: Oct. 12, 1993

[54] ELECTROLYTIC PUMP

[75] Inventor: Frank A. Ludwig, Rancho Palos Verdes, Calif.

[73] Assignee: Hughes Aircraft Company, Los Angeles, Calif.

[21] Appl. No.: 963,185

[22] Filed: Oct. 19, 1992

[51] Int. Cl.$^5$ .............................................. C25B 11/03
[52] U.S. Cl. .................................... 204/228; 204/237; 204/273; 204/278; 204/400; 204/290 F; 204/292; 204/294; 204/434; 204/153.1
[58] Field of Search ............... 417/48, 54, 55, 108; 204/234, 237, 261, 273, 278, 228, 400, 434, 153.1

[56] References Cited

U.S. PATENT DOCUMENTS

| | | | |
|---|---|---|---|
| 3,222,269 | 12/1965 | Stanton | 204/278 X |
| 3,539,486 | 11/1970 | Fleck | 204/237 X |
| 3,654,119 | 4/1972 | White et al. | 204/228 |
| 3,785,954 | 1/1974 | Herbert | 204/228 |
| 3,897,173 | 7/1975 | Mandroian | 417/240 X |
| 4,105,528 | 8/1978 | Hasebe | 204/237 |
| 4,379,043 | 4/1983 | Chappele | 204/278 X |

Primary Examiner—Richard E. Gluck
Attorney, Agent, or Firm—M. E. Lachman; M. W. Sales; W. K. Denson-Low

[57] ABSTRACT

An apparatus and method for producing an adjustable constant flow of electrochemical fluid. The apparatus is designed for use in an in-tank electrochemical plating bath sensor. The apparatus and method utilize pumping electrodes placed within an electrode chamber. An electrical potential is applied to the electrodes to produce a gaseous stream which produces vertical movement of the electrochemical fluid through the electrode chamber. The voltage applied to the electrodes is periodically reversed in order to prevent the buildup of metal deposits.

15 Claims, 3 Drawing Sheets

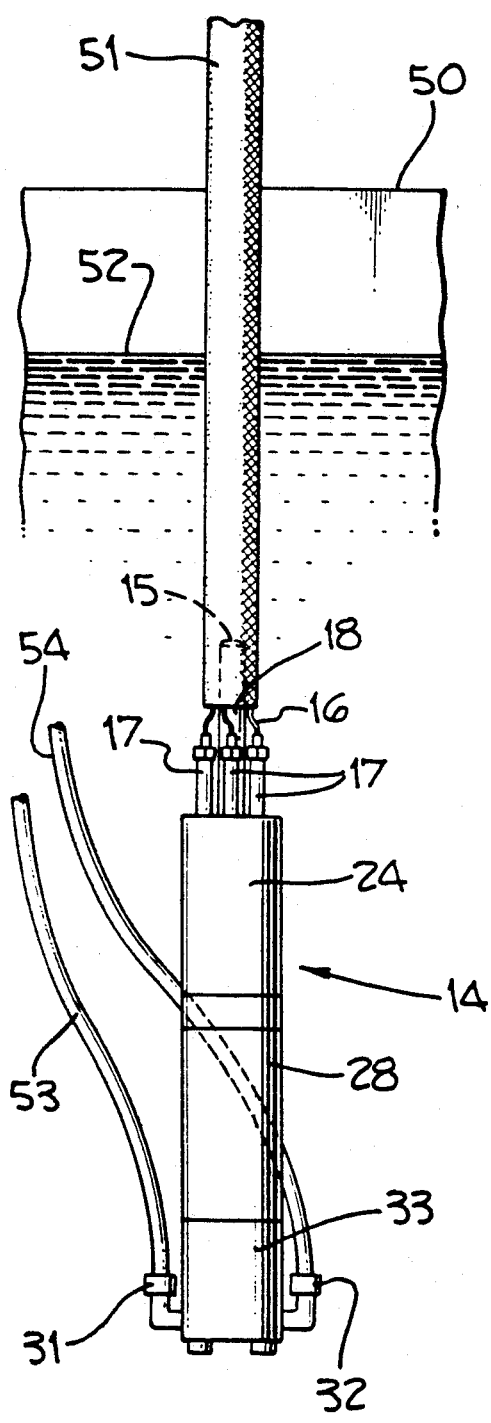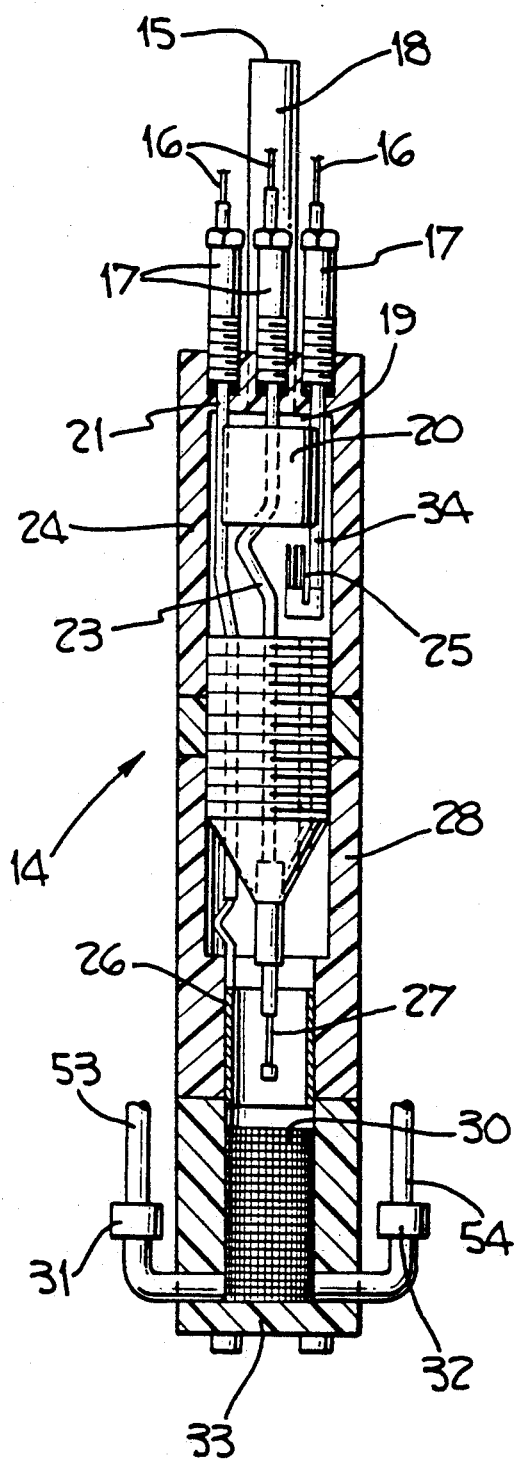

ELECTROLYTIC PUMP

This invention was made with United States Government support under Contract Number DAAB07-88-C-A047 awarded by the Department of the Army. The United States Government has certain rights in this invention.

BACKGROUND OF THE INVENTION

1. Field of the Invention

The present invention relates generally to electrolytic pumps for electrochemical fluids. More particularly, the present invention relates to an electrolytic pump which is adapted for use in an in-tank plating bath electrochemical sensor. The pump is designed to provide an adjustable constant flow of electrochemical fluid through the sensor, such flow being of the type which is required for optimal measurement and analysis of the electrochemical properties of the fluid.

2. Description of Related Art

Pump requirements for circulating fluids through the sensors used in plating bath analysis methods, such as the method disclosed in U.S. Pat. No. 4,631,116, which is assigned to the present common assignee, are typically met by using an externally mounted or submerged mechanical pump which is connected to the sensor via a network of tubing (see col.6, lines 2414 29). Alternatively, a "fish tank" type of pump requiring tubing, an air supply, and an air metering device could be used.

As was noted in U.S. Pat. No. 4,631,116, agitation of the electrolytic solution at the sensor creates turbulent conditions which decrease the sensitivity of the analysis method and its ability to resolve fine structure (see col.15, lines 17-18). In response to this problem, in-tank electrochemical sensors have been developed in which the sensor measurement electrodes are housed in a tube which is submerged within the plating solution. The solution could thus be drawn past the sensors at specified flow rates, and experimentation with the sensors has shown that using a medium flow rate optimized the performance of the electrochemical fluid analysis system. This optimal flow rate is maintained by the pump.

However, the current pumping methods described above are expensive and typically require frequent and costly maintenance. The tubing must be replaced quite often, and the pump itself is vulnerable to breakdown. Production costs associated with the use of in-tank sensors are thus significantly higher as a result of the limitations inherent in the currently available pumping techniques.

In addition, the currently utilized pumps consume considerable amounts of power in the course of continuous operation of a plating bath analysis system. This contributes to higher energy costs and resultant higher production costs.

Furthermore, the current external or submerged mounting of the pump and the required tubing is awkward and complicates the equipment associated with the plating bath setup. In the case of the externally mounted pump, this extra equipment is visually unappealing and represents a potential hazard to those working in and around the plating area.

As is apparent from the above, there presently is a need for a rugged, inexpensive, low maintenance and limited power consumption electrolytic pump. Further, the pump should require no external or submerged motor or tubing. The pump should include all of these features and still be able to draw fluid through the body of the electrochemical sensor at the desired optimal flow rates.

SUMMARY OF THE INVENTION

In accordance with the present invention an electrolytic pump apparatus and method are provided which are particularly well-suited for use with an in-tank electrochemical sensor. The electrolytic pump consists of an electrode chamber through which fluid passes, pumping electrodes, and a control circuit for supplying power to the pumping electrodes. The control circuit powers the electrodes such that one of the pumping electrodes is positively charged relative to the electrochemical fluid, while the other pumping electrode is negatively charged. These charges allow the electrodes to electrolyze the electrochemical fluid, producing a stream of gas within the electrode chamber which provides for movement of the fluid through the electrode chamber.

As a further feature of the present invention, the polarity of the charge on the pumping electrodes is periodically reversed in order to prevent buildup of deposits from the electrochemical fluid at the pumping electrodes. This reversal extends the operating life of the pumping electrodes and considerably reduces the need for pump maintenance or replacement.

As another feature of the present invention, the velocity of fluid flow through the sensor is maintainable at a constant rate, and this rate may be easily and quickly adjusted by varying the current applied to the pumping electrodes. The pump is thus designed to maintain the optimal fluid flows required for accurate plating bath analysis. The fluid is drawn through the sensor probe at the desired medium flow rates with minimal agitation, improving the accuracy of plating bath analysis methods.

In accordance with the present invention, the pump is an integral part of the electrochemical sensor and therefore requires no external or submerged mounting or tubing to connect it with the sensor. Using the stream of gas to propel the fluid through the sensor reduces energy costs which are normally associated with the operation of a mechanical or air supply pump. For example, pumps in accordance with the present invention consume on the order of 3 watts of power.

Maintenance problems normally associated with external or submerged pumps essentially disappear in the present invention, resulting in lower production costs for users of plating baths. In addition, integrating the pump into the sensor overcomes the problems of awkwardness, complexity, and unattractiveness normally associated with the traditional pumping techniques, and further serves to minimize potential hazards in the work area.

The above-discussed features and attendant advantages of the present invention will become better understood by reference to the following detailed description of the preferred embodiments and the accompanying drawings.

BRIEF DESCRIPTION OF THE DRAWINGS

FIG. 2 is a side view of an electrochemical sensor immersed in a plating bath and incorporating a pre- FIG. 3 is a side sectional view of the electrochemical sensor of FIG. 2 showing the general location of the electrolytic pump within the sensor.

DETAILED DESCRIPTION OF THE PREFERRED EMBODIMENTS

Exemplary electrochemical analysis methods and equipment to which the electrolytic pump of the present invention is connected are described in U.S. Pat. No. 4,631,116, which has been previously discussed. The contents of this patent are hereby expressly incorporated by reference. It has been determined that the accuracy of plating bath analysis methods such as those described in U.S. Pat. No. 4,631,116 are enhanced through the use of an in-tank sensor in which a regulated constant velocity fluid flow past the sensing electrodes is maintained. An exemplary sensor 14 suitable for use with the techniques described in U.S. Pat. No. 4,631,116 is shown in FIG. 2.

Figure 1:
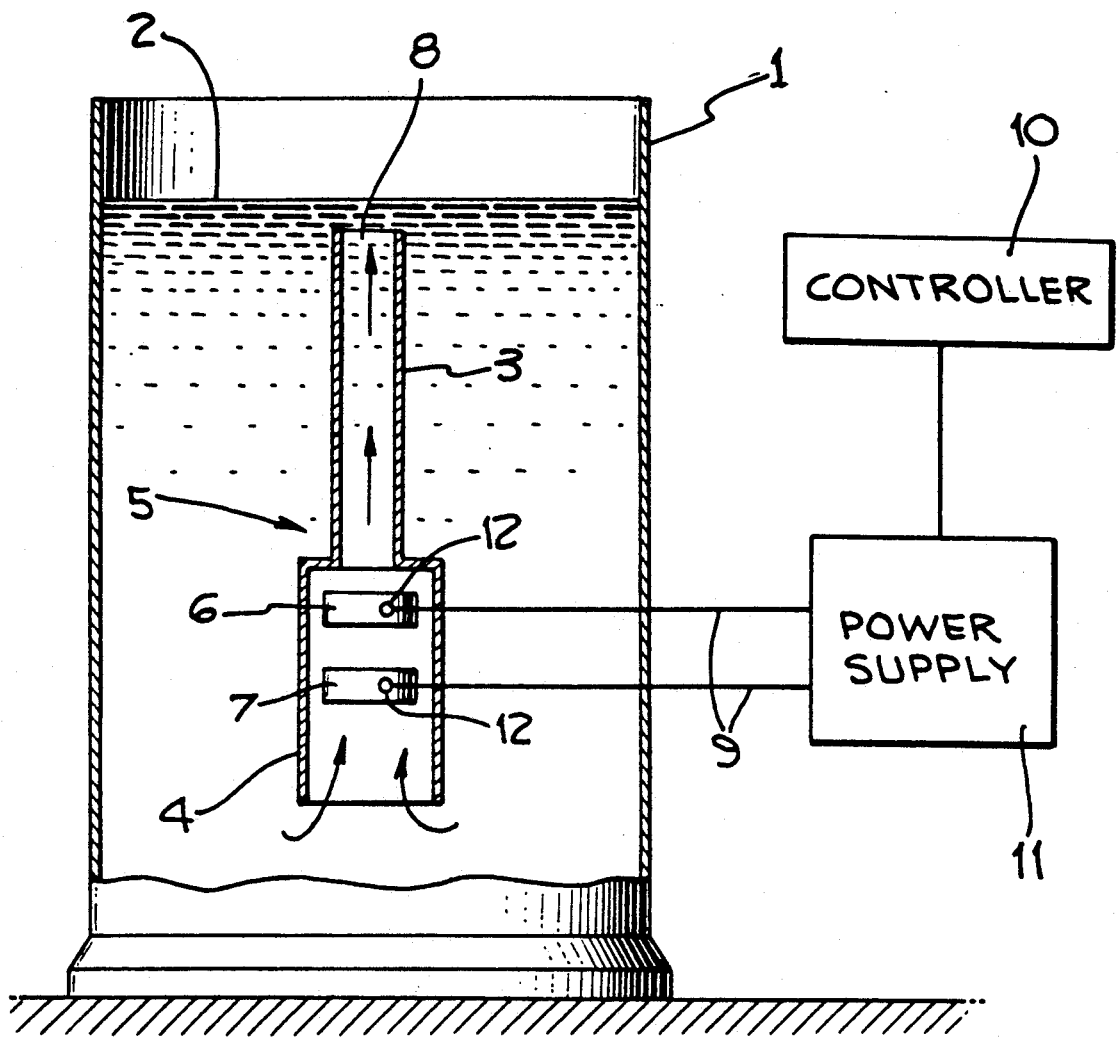
FIG. 1 is a side view of a preferred embodiment of the electrolytic pump used to demonstrate its functionality and sensitivity to variation in pump parameters.

FIG. 1 shows a side view of a preferred embodiment of the electrolytic pump. A pump 5 consisting of an electrode chamber 4 and an outlet tube 3 is immersed in a container 1 filled with electrochemical fluid 2. The term "electrochemical fluid" is used herein to mean any fluid which has electrical conductivity sufficient to sustain the required pumping current and which can be electrolyzed to produce a gaseous reaction product at, at least, one electrode. The pumping electrode chamber 4 contains pumping electrodes 6, 7 formed in a cylindrical shape from a conductive material such as platinum, silver, gold, tantalum, treated graphite, vitreous carbon, or other conductive material which is relatively inert with respect to the electrochemical fluid. The pumping electrodes are separated by a distance of about 0.5 to 2.0 centimeters, and are located from about 10 to 50 centimeters below the top 8 of the outlet tube 3. One of the electrodes serves as an anode and the other as a cathode. The electrodes 6, 7 are connected to an external power supply 11 via wires 9 and electrical contacts 12. The power supply output can be varied by a controller 10. The electrochemical fluid 2 within the pumping electrode chamber 4 is electrolyzed by the current applied to the pumping electrodes such that a stream of gas is produced which rises up through the outlet tube 3 and pulls fluid along with it. Thus the continuous energization of the pumping electrodes produces a movement of fluid upward through the electrode chamber 4 and outlet tube 3 as indicated by the arrows in FIG. 1.

The outlet tube 3 of the electrolytic pump 5 should be submerged below the electrochemical fluid 2 surface level in order to minimize the pumping pressure. The electrode chamber 4 and outlet tube 3 are preferably cylindrical in shape, with an inner diameter of between approximately 0.5 and 2.0 centimeters, and are made of a material which is compatible with the electrochemical fluid being used, such as a plastic material, of which Teflon is a preferred material. In this preferred embodiment the electrode chamber 4 has a wider diameter than the outlet tube 3 but it should be understood that other embodiments may be constructed with different proportions to achieve substantially the same result. For example, the pumping electrode chamber and outlet tube could both be part of a single tube with a constant diameter.

For aqueous plating solutions the majority of the gas is produced at the anode in the form of oxygen gas, while the cathode produces a small amount of hydrogen gas. Some chlorine gas is also produced at the anode in solutions containing chloride ions. In order to effect the electrolysis it is preferable that a constant current of about 1.5 amperes be applied to the electrodes. This current flow will usually require about 1.5 to 3.0 volts.

The rate of fluid flow through the pump is easily and accurately controlled by adjusting the amount of current applied from the external power supply 11. An applied current of between about 0.5 and 4.0 amperes is adequate to establish proper flow rates for most plating fluid analysis systems. The polarity of the applied voltage should be periodically reversed for a period of time typically on the order of one to sixty seconds through the use of a power supply controller 10 to prevent the buildup of deposits at any particular electrode. A reversal time of 15 to 30 seconds is adequate for most electrochemical solutions. The reversal time may be shortened where higher pumping electrode currents are used.

The exact size of the pumping electrodes is not critical. A smaller area may be advantageous in that a lower precious metal cost will result, as well as higher efficiency in hydrogen gas production. However, too small an area may allow the plating to become burnt and non-adherent, or prevent it from being reoxidized. As a result, the plating may fall away from the electrode and accumulate in the sensor in which the pump is installed, potentially interfering with measurements. In view of these tradeoffs, platinum electrodes with about a three square centimeter area are used in the preferred embodiment. If the electrolytic bath is corrosive to platinum, however, the electrode area should be increased and the reversal time increased to at least 30 seconds.

A pump of the type shown in FIG. 1 was operated to determine the sensitivity of the pump to variations in several of the pump parameters. A measuring cup was located at the top of the outlet tube to collect and measure the fluid passing through the pump. These fluid collection measurements were checked by setting the outlet tube slightly below the fluid surface, measuring the height of the pumped effluent above the fluid level, and comparing it to the height of pumped effluent generated by a mechanical pump set at a known flow rate. The two methods resulted in measurements repeatable within 6%.

The following operating parameters were established for the above system: 1) increasing the diameter of outlet tube 3 increases the flow rate for a given current; 2) increasing the length of outlet tube 3 increases the flow rate for a given current; 3) applying a larger current to the pumping electrodes 6, 7 will produce a higher flow rate; 4) the flow rate produced by the application of AC current to the pumping electrodes is not significantly different from the rates produced via the application of DC current; and 5) less than two amperes of applied current is required to produce optimal flow rates for most electrochemical plating solutions.

Based on the above results, a preferred electrolytic pump will have a cylindrical electrode chamber with an inside diameter of about 1.5 to 2.0 centimeters, will have a cylindrical outlet tube with an inside diameter of about 1.0 to 1.5 centimeters opening at the top, with platinum electrodes of about three square centimeter area each located about 1.0 centimeter apart and about 18 to 25 centimeters below the top of the outlet tube, and will use currents of approximately 1.5 amperes reversing about every 15 seconds. This preferred arrangement produces flow rates on the order of 150 to 300 milliliters per minute, yielding near optimal results for most plating solutions using analytical methods such as those described in U.S. Pat. No. 4,631,116.

An exemplary electrochemical sensor 14 incorporating the present invention is shown immersed in a tank 50 of electroplating fluid 52 in FIG. 2. A side sectional view of this sensor 14 indicating the location of the electrolytic pump 20 within the sensor is shown in FIG. 3. The sensor 14 contains sensing electrodes 26, 27 and reference electrode 25 connected to external powering means via internal wires 21, 23 and 34, respectively, and external wires 16 which enter the sensor through leak-proof bushings 17. The external wires are covered and supported by shielding tube 51. The electrolytic pump is installed within the sensor at the location indicated by 20 at the interior 19 of the fluid exit chamber 24.

Figure 5:
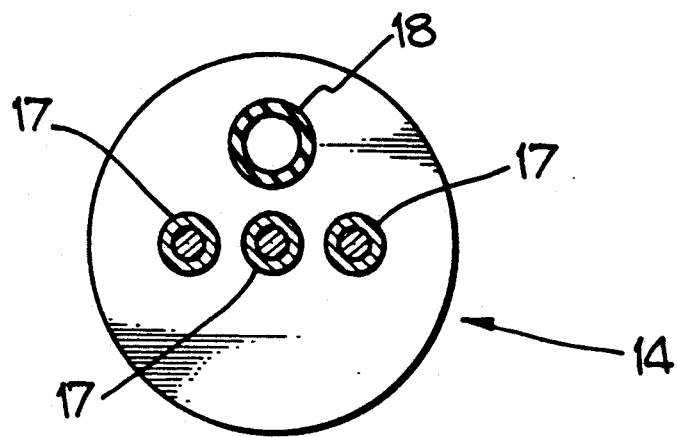
FIG. 5 is sectional view taken in the plane 5-5 of FIG. 4.

In operation, the pump shown generally at 20 draws electroplating fluid 52 into the sensor 14 through tubes 53, 54 and inlets 31, 32. The fluid is then drawn through the flow damper screen 30 within the fluid flow control chamber 33 and into the sensing chamber 28 where it passes the sensing electrodes 26, 27. The fluid then exits the sensor through fluid exit chamber 24 and is delivered back into the tank via the top 15 of the fluid exit chamber outlet tube 18. The fluid exit chamber 24 and fluid exit chamber outlet tube 18 in FIG. 3 are alternative embodiments of the electrode chamber 4 and outlet tube 3 shown in FIG. 1. FIG. 5 shows a sectional view of sensor 14 along the plane 5—5 of FIG. 4 which illustrates the placement of the fluid exit chamber outlet tube 18 in relation to the bushings 17 through which the external electrode wires 16 pass into the sensor.

Figure 4:
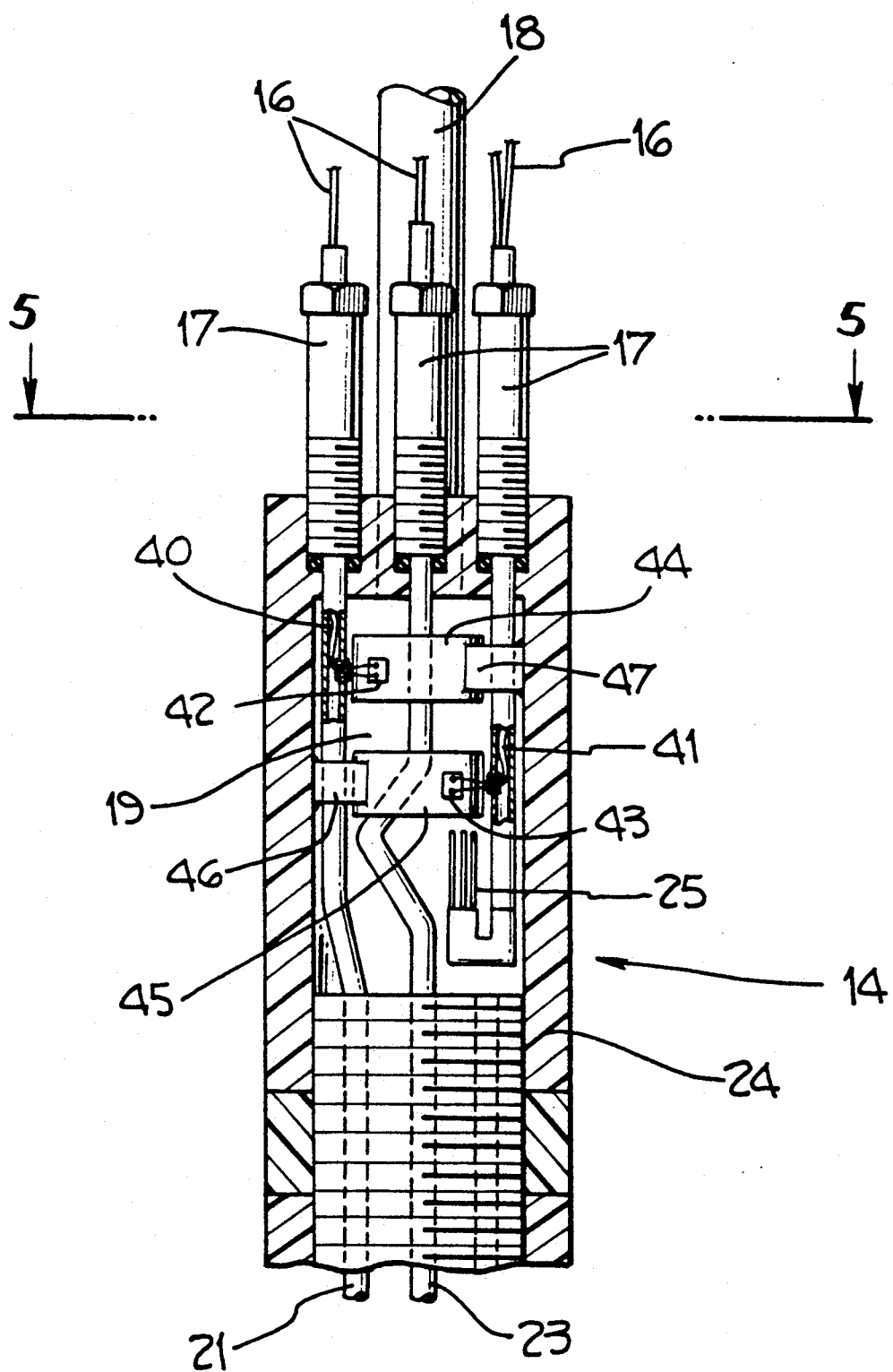
FIG. 4 is an enlarged detail view of the electrode chamber.

A more detailed side sectional view of the electrolytic pump 20 located within the preferred exemplary sensor 14 is shown in FIG. 4. The electrolytic pump 20 consists of two pumping electrodes 44, 45 which are connected to an external power source via wires 40, 41. The pumping electrodes are supported within the sensor by non-conducting brackets 46, 47 which secure the electrodes to the inner wall of the sensor. Wires 40, 41 make electrical contact with the pumping electrodes at contacts 42, 43. The pumping electrodes 44, 45 are preferably formed of platinum, silver, gold or tantalum. Other electrodes such as chrome plated nickel, treated graphite or vitreous carbon could be used for some plating solutions. The pumping electrodes are preferably cylindrical in shape, and located about 0.5 to 1.5 centimeters apart. An electrical current is applied to the pumping electrodes by the external power source such that one pumping electrode serves as an anode and the other as a cathode. This energization serves to electrolyze the electroplating fluid such that a stream of gas is produced which pulls the fluid into and through the sensor 14 at a rate which is dependent upon the current applied to the pumping electrodes.

The pumping electrodes 44, 45 which generate the gas stream are preferably located in the sensor 14 above the sensing electrodes 26, 27 and reference electrode 25 such that the rising gas generated by the pumping electrodes 44, 45 will not interfere with the measurements taken by the sensor 14 in the course of analyzing the fluid in the plating bath.

It is important that the pumping electrodes 44 and 45 be electrically isolated from the sensing and reference electrodes 26, 27 and 25. This can be done by floating the pumping electrodes 44 and 45 and not connecting them to ground. Alternatively, a separator disk with a small connecting hole may be placed between the two electrode systems. Optionally, the reference electrode system can be relocated in the sensing chamber 28 to remove it from the pumping electrodes.

Although the present description has been limited to pumping of aqueous electroplating fluids, it will be understood by those skilled in the art that the present invention may be applied to different types of fluids for which electrochemical monitoring is desired. Preferably, the fluid being pumped will be an aqueous solution wherein oxygen is the principle gas being generated. However, other fluids may be used which are capable of generating gas when subjected to an electric potential. The term "electrochemical fluid" when used herein is intended to cover any of the above fluids for which monitoring of one or more electrochemical, analytical or other quality properties is desired.

It will be understood by those skilled in the art that the foregoing disclosures are by way of example only, and that many alternate constructions are possible without deviating from the scope of the invention, which is limited only by the appended claims.

What is claimed is:

1. An electrolyte pump apparatus adapted for use with an in-tank electrochemical sensor wherein said sensor includes at least one sensing electrode, said electrolytic pump apparatus comprising:

an electrode chamber having a top end and a bottom end through which electrochemical fluid is passed from said bottom end to said top end;

at least two pumping electrodes located within said electrode chamber and above said sensing electrode; and control means for applying sufficient voltage to said pumping electrodes such that at least one of said electrodes is positively charged relative to the electrochemical fluid while at least one of the other electrodes is negatively charged relative to the electrochemical fluid, wherein said charged pumping electrodes electrolyze the electrochemical fluid within said electrode chamber to produce a gaseous stream within said electrode chamber, said gaseous stream flowing toward said electrode chamber top end to thereby provide for movement of fluid through said electrode chamber while preventing said gaseous stream from interfering with the sensing electrode measurements.

2. The apparatus of claim 1 further including an outlet tube connected to the top end of said electrode chamber through which fluid moves as a result of said gaseous stream.

3. The apparatus of claim 1 wherein said control means further include switching means for selectively applying voltages to said pumping electrodes such that the polarity of each of the electrodes periodically alternates between positive and negative thereby preventing the accumulation of deposits from the electrochemical fluid on the electrodes.

4. The apparatus of claim 1 wherein said control means further includes current control means for varying the current applied to said pumping electrodes to provide control of the amount of gas generated to form said gaseous stream to thereby control the velocity of electrochemical fluid flow through said electrode chamber.

5. The apparatus of claim 1 wherein said electrode chamber is in the shape of a cylinder having a diameter of between about 0.5 and 2.0 centimeters.

6. The apparatus of claim 1 wherein the pumping electrodes are cylindrical in shape.

7. The apparatus of claim 1 wherein the pumping electrodes are located from about 0.5 to 2.0 centimeters apart.

8. The apparatus of claim 1 wherein said pumping electrodes consist essentially of a conductive material selected from the group consisting of platinum, silver, gold, tantalum, treated graphite, and vitreous carbon.

9. The apparatus of claim 2 wherein said pumping electrodes are located between about 10 and 50 centimeters below the top of the outlet tube.

10. A method for pumping electrochemical fluid, said method comprising:
providing an electrode chamber having a top end and a bottom end through which electrochemical fluid is passed from said bottom end to said top end;
providing at least two pumping electrodes located within said electrode chamber and within an in-tank electrochemical sensor, said in-tank electrochemical sensor including at least one sensing electrode wherein said pumping electrodes are located above said sensing electrode; and
applying a sufficient voltage to said pumping electrodes such that at least one of said electrodes is positively charged relative to the electrochemical fluid while at least one of the other electrodes is negatively charged relative to the electrochemical fluid, wherein said voltage applied to said pumping electrodes is sufficient to electrolyze the electrochemical fluid within said electrode chamber to produce a gaseous stream within said electrode chamber, said gaseous stream flowing toward said electrode chamber top end to thereby provide for movement of fluid through said electrode chamber, while preventing said gaseous stream from interfering with the sensing electrode measurements.

11. The method of claim 10 wherein said electrode chamber is completely submerged in said electrochemical fluid.

12. The method of claim 16 wherein the polarity of each of the pumping electrodes is periodically switched between positive and negative.

13. The method of claim 16 wherein the velocity of electrochemical fluid flow through said electrode chamber is adjusted by varying the current applied to said pumping electrodes.

14. The method of claim 13 wherein the current applied to the pumping electrodes is between about 0.5 and 4.0 amperes.

15. The method of claim 12 wherein the polarity of each pumping electrode is reversed every one to sixty seconds.

* * * * *